US012569337B2

(12) United States Patent
Lombardi et al.

(10) Patent No.: US 12,569,337 B2
(45) Date of Patent: Mar. 10, 2026

(54) PROSTHETIC VALVE, DELIVERY APPARATUS AND DELIVERY METHOD

(71) Applicant: Symetis SA, Ecublens (CH)

(72) Inventors: Fabien Lombardi, Prilly (CH); Youssef Biadillah, Geneva (CH); Jean-Luc Hefti, Cheseaux-Noreaz (CH); Luc Mantanus, Lausanne (CH); Stephane Delaloye, Bulach (CH)

(73) Assignee: Symetis SA, Ecublens (CH)

( * ) Notice: Subject to any disclaimer, the term of this patent is extended or adjusted under 35 U.S.C. 154(b) by 0 days.

(21) Appl. No.: 18/216,761

(22) Filed: Jun. 30, 2023

(65) Prior Publication Data

US 2023/0338141 A1     Oct. 26, 2023

Related U.S. Application Data

(63) Continuation of application No. 16/383,583, filed on Apr. 13, 2019, now Pat. No. 11,793,636, which is a
(Continued)

(30) Foreign Application Priority Data

Feb. 6, 2013     (EP) ..................................... 13000597
Oct. 28, 2013     (EP) ..................................... 13190533

(51) Int. Cl.
*A61F 2/24*          (2006.01)
*A61F 2/97*          (2013.01)
(52) U.S. Cl.
CPC .......... *A61F 2/2427* (2013.01); *A61F 2/2436* (2013.01); *A61F 2/2418* (2013.01); *A61F 2/97* (2013.01)

(58) Field of Classification Search
CPC .... A61F 2/2427; A61F 2/2436; A61F 2/2418; A61F 2/97
See application file for complete search history.

(56) References Cited

U.S. PATENT DOCUMENTS

2010/0049313 A1     2/2010     Alon et al.
2011/0098805 A1     4/2011     Dwork et al.
(Continued)

FOREIGN PATENT DOCUMENTS

WO     2007047488 A2     4/2007
WO     2007071436 A2     6/2007
(Continued)

OTHER PUBLICATIONS

International Search Report and Written Opinion, mailed May 15, 2014, for International Application No. PCT/EP2014/052311.
(Continued)

*Primary Examiner* — Brooke Labranche
(74) *Attorney, Agent, or Firm* — Seager, Tufte & Wickhem LLP

(57)          ABSTRACT

A delivery catheter for a prosthetic heart valve, the valve expandable from a collapsed condition for delivery to an expanded condition for implantation, the delivery catheter comprising: a holder for engaging the valve in the collapsed state of the valve, the holder configured such that (i) in response to a radial compression force exerted thereon, the holder has a first shape defining an exposed engagement region for engaging at least a portion of the collapsed prosthetic heart valve for restraining axial displacement of the prosthetic valve in at least one axial direction of the catheter, and (ii) in response to removal of the radial compression force upon expansion of the valve, at least a portion of the holder transitions to a second shape.

11 Claims, 10 Drawing Sheets

Related U.S. Application Data continuation of application No. 14/766,417, filed as application No. PCT/EP2014/052311 on Feb. 6, 2014, now Pat. No. 10,285,811.

(56) References Cited

U.S. PATENT DOCUMENTS

| | | |
|---|---|---|
| 2011/0264202 A1 | 10/2011 | Murray, III et al. |
| 2012/0078350 A1 | 3/2012 | Wang et al. |
| 2012/0290078 A1 | 11/2012 | Bourang et al. |
| 2013/0274870 A1 | 10/2013 | Lombardi et al. |

FOREIGN PATENT DOCUMENTS

| | | |
|---|---|---|
| WO | 2009053497 A1 | 4/2009 |
| WO | 2011025945 A1 | 3/2011 |
| WO | 2011153210 A1 | 12/2011 |
| WO | 2012009006 A1 | 1/2012 |
| WO | 2012032187 A1 | 3/2012 |
| WO | 2012038550 A1 | 3/2012 |

OTHER PUBLICATIONS

International Preliminary Report on Patentability, mailed Aug. 20, 2015, for corresponding PCT Application No. PCT/EP2014/052311.

Van Mieghem et al., "Incidence, Timing and Predictors of Valve Dislodgement During TAVI with the Medtronic Core Valve System," Catheterization and Cardiovascular Interventions, 6 pages, Jul. 29, 2011. Accessed Sep. 5, 2023. (Abstract Only).

PROSTHETIC VALVE, DELIVERY APPARATUS AND DELIVERY METHOD

CROSS-REFERENCE TO RELATED APPLICATIONS

This application claims priority to U.S. application Ser. No. 16/383,583, filed Apr. 13, 2019, which is a continuation of U.S. application Ser. No. 14/766,417, filed Aug. 6, 2015, which claims priority to International Patent Application No. PCT/EP2014/052311, filed Feb. 6, 2014, and entitled "Prosthetic Valve, Delivery Apparatus and Delivery Method," which in turn claims priority to European Patent Application No. 13000597.8, filed Feb. 6, 2013 and European Patent Application No. 13190553.1, filed Oct. 28, 2013. The present application incorporates herein by reference the disclosures of each of the above-referenced applications in their entireties.

TECHNICAL FIELD

The present disclosure is directed to a device for valve replacement, especially of a cardiac valve, for example, the aortic valve. Further the present disclosure is directed to a delivery device and to a method of operation of a delivery device. A valve replacement device may also be referred to as a stent-valve or a valved stent.

BACKGROUND

Traditional approaches for aortic valve replacement require the cutting of a relatively large opening in the patient's sternum ("sternotomy") or thoracic cavity ("thoracotomy") in order to allow a surgeon to access a patient's heart. Additionally, these approaches require arrest of the patient's heart and a cardiopulmonary bypass (i.e., use of a heart-lung bypass machine to oxygenate and circulate the patient's blood). In recent years, efforts have been made to reduce invasiveness by using a transcatheter procedure, namely by delivering and implanting a valve replacement device via a catheter inserted through a smaller skin incision, using either a transvascular access or a transapical access to the valve implantation site.

Such valve replacement devices and delivery systems for placing a replacement valve via a catheter are known in the art, and are disclosed, for example, in WO 2007/071436, WO 2009/053497, WO 2011/153210, WO 2012/032187 and WO 2012/038550, While less invasive and arguably less complicated, transcatheter heart valve replacement devices and procedures still face various difficulties. One difficulty is the possibility of dislodgement of the prosthetic valve from its intended implantation position during the procedure. As reported in the article "Incidence, Timing and Predictors of Valve Dislodgement During TAVI With the Medtronic CoreValve System", Nicolas M. Van Mieghem et al, (Catheterization and Cardiovascular Interventions 00:000-000 (2011), Wiley) such dislodgement is a non-rare occurrence. Dislodgement was reported to occur in 18% of procedures analysed, and others' studies of dislodgement in 10% and in 22% of cases are also referred to. When a prosthetic valve is implanted within a beating heart, there may be some risk of dislodgement. Factors affecting risk of dislodgement may include: heart motion with respect to the delivery catheter to which the valve is attached during implantation; blood flow acting on the prosthesis; malpositioning of the prosthesis (for example, too high or too low); incorrect sizing of the prosthesis with respect to the native valve being replaced; pulling on the delivery catheter when the stent frame has remained attached to the delivery catheter; sticking of the catheter against the prosthetic framework while in the left ventricle outflow tract.

SUMMARY

Although not limiting, at least some of the ideas in the present disclosure have been devised bearing the above issues in mind. Such ideas may solve or alleviate at least one of the above issues.

Broadly speaking, in one non-limiting aspect, a delivery catheter is disclosed for an expandable prosthetic heart valve, the valve expandable from a collapsed condition for delivery to an expanded condition for implantation. The delivery catheter may further comprise any one or more of the following features, which are all optional:

(a) The delivery catheter may comprise a holder including an engagement region for engaging at least a portion of the prosthetic heart valve for restraining axial displacement of the prosthetic valve in at least one axial direction of the catheter, for example, when the valve is in the collapsed condition around the holder.

(b) The delivery catheter may comprise at least one fender, the fender transitioning from a non-deployed state during delivery of the collapsed valve, to a deployed state upon expansion of the valve.

The fender may be movable and/or deformable when transitioning from the non-deployed state to the deployed state. The fender may be transitioned reversibly between the two states.

In some embodiments, in the non-deployed state the fender permits engagement between the engagement region and the collapsed valve, and/or in the deployed state the fender urges at least the engagement region of the holder away from engagement with the expanded valve.

In some embodiments, the fender may be biased to the deployed state, and may be transitioned (e.g. be collapsible) to the non-deployed state against the effect of the bias. In some embodiments, the fender may be of or comprise one or more of: resilient material; elastic material; pseudo-elastic material; shape-memory material (for example shape-memory alloy).

In some embodiments, the fender is carried by the holder and/or is part of the holder.

(c) The delivery catheter may comprise a separator for bearing against the valve to urge the engagement region of the holder to separate from the valve upon expansion of the valve.

In some embodiments, the separator transitions from a non-deployed state (e.g. allowing engagement between the valve and the engagement region), to a deployed state (e.g. urging the engagement region to separate from the valve). The separator may bear against the valve in at least one of the states (e.g. the deployed state), and optionally in both states.

The separator may be movable and/or deformable when transitioning from the non-deployed state to the deployed state. The separator may be transitioned reversibly between the two states.

In some embodiments, the separator may be biased to the deployed state, and may be transitioned (e.g. be collapsible) to the non-deployed state against the effect of the bias. In some embodiments, the separator may be of or comprise one or more of: resilient material; elastic material; pseudo-elastic material; shape-memory material (for example shape-memory alloy).

In some embodiments, the separator is carried by the holder and/or is part of the holder.

The same elements may optionally represent both the separator, and the aforementioned fender (if implemented).

(d) The delivery catheter may comprise a disengagement device for bearing against the valve to disengage the valve relative to the engagement region upon expansion of the valve. The disengagement device may be configured to eject the valve clear of the engagement region.

For example, the disengagement device may be or comprise an ejector for ejecting the valve with respect to the engagement region. The ejector may be configured to eject the valve clear of the engagement region.

In some embodiments, the disengagement device (e.g. ejector) transitions from a non-deployed state (e.g. allowing engagement between the valve and the engagement region), to a deployed state (e.g. ejecting the valve from the engagement region). The disengagement device (e.g. ejector) may bear against the valve in at least one of the states (e.g. the deployed state), and optionally in both states.

The disengagement device (e.g. ejector) may be movable and/or deformable when transitioning from the non-deployed state to the deployed state. The disengagement device (e.g. ejector) may be transitioned reversibly between the two states.

In some embodiments, the disengagement device (e.g. ejector) may be biased to the deployed state, and be transitioned (e.g. be collapsible) to the non-deployed state against the effect of the bias. In some embodiments, the disengagement device (e.g. ejector) may be of or comprise one or more of: resilient material; elastic material; pseudo-elastic material; shape-memory material (for example shape-memory alloy).

In some embodiments, the disengagement device (e.g. ejector) is carried by the holder and/or is part of the holder.

The same elements may optionally represent the disengagement device (e.g. ejector) and/or the aforementioned separator (if implemented) and/or the aforementioned fender (if implemented).

(e) The delivery catheter may further comprise a cage associated with at least the engagement region of the holder. The cage may transition from a non-deployed state in which the cage does not substantially and/or does not functionally obscure the engagement region, to a deployed state in which the cage substantially and/or functionally obscures (e.g. shrouds) the engagement region.

The cage may be defined by a single member, or by two or more members in combination.

The cage may be movable and/or deformable when transitioning from the non-deployed state to the deployed state. The cage may be transitioned reversibly between the two states.

In some embodiments, the cage may be biased to the deployed state, and be transitioned (e.g. be collapsible) to the non-deployed state against the effect of the bias. In some embodiments, the cage may be of or comprise one or more of: resilient material; elastic material; pseudo-elastic material; shape-memory material (for example shape-memory alloy).

In some embodiments, the cage is carried by the holder and/or is part of the holder.

The same elements may optionally represent the cage, and/or the disengagement device (e.g. ejector) if implemented, and/or the aforementioned separator (if implemented) and/or the aforementioned fender (if implemented).

(f) The holder may comprise at least one element biased to transition from a non-deployed state in which the element does not substantially project outwardly with respect to a portion of the holder, to a deployed state in which the element project substantially outwardly with respect to a portion of the holder.

The portion of the holder may be the engagement region.

The at least one element may exert a bias force for separating the respective portion of the holder from the valve upon valve expansion.

The at least one element may be movable and/or deformable when transitioning from the non-deployed state to the deployed state. The at least one element may be transitioned reversibly between the two states In some embodiments, the at least one element may be biased to the deployed state, and be transitioned (e.g. be collapsible) to the non-deployed state against the effect of the bias. In some embodiments, the at least one element may be of or comprise one or more of: resilient material; elastic material; pseudo-elastic material; shape-memory material (for example shape-memory alloy).

The same elements may optionally represent the at least one element, and/or the aforementioned cage (if implemented) and/or the aforementioned disengagement device (e.g. ejector) and/or the aforementioned separator (if implemented) and/or the aforementioned fender (if implemented).

(g) The engagement region of the holder may comprise one or more male and/or female engagement regions for mating and/or interlocking engagement with the prosthetic valve. The engagement region, and an element defining a stop surface associated with the engagement region, may be relatively movable with respect to each other. For example, in the case of a male engagement region, the relative movement may vary the functional projection height with respect to the stop surface. For example, in the case of a female engagement region, the relative movement may vary the functional depth with respect to the stop surface.

In some embodiments, the engagement region may be generally fixed, and the element defining the stop surface may be movable.

In some embodiments, the engagement region may comprise a male engagement region in the form of a projection, and the element defining the stop surface may have an aperture through which the projection protrudes. The projection and element may be relatively movable between a stowed condition in which a majority of the height of the projection protrudes proud of the stop surface, and a deployed condition in which a majority of the height of the projection does not protrude proud of the stop surface. The engagement region and the element defining the stop surface, may be biased relative to each other towards the deployed condition.

The element defining the stop surface may be of or comprise one or more of: resilient material; elastic material; pseudo-elastic material; shape-memory material (for example shape-memory alloy).

In some embodiments, the element defining the stop surface is carried by the holder and/or is part of the holder.

The same elements may optionally represent the element defining the stop surface, and/or the aforementioned cage (if implemented), and/or the aforementioned at least one element (if implemented), and/or the disengagement device (e.g. ejector) if implemented and/or the aforementioned separator (if implemented) and/or the aforementioned fender (if implemented).

(h) The delivery catheter may further comprise a deployable ramp for shrouding the engagement region and/or permitting axial sliding between the valve and the holder when the ramp is deployed. The ramp may be biased to a deployed state, and be transitioned (e.g. be collapsible) to a non-deployed state in response to a radial compression force applied to the holder and/or deployable ramp. For example, the ramp may be transitioned to the non-deployed state upon collapsing of a valve around the holder.

(i) As an alternative to (a), the delivery catheter may comprise a holder for engaging the valve in the collapsed state of the valve. The holder may be configured such that (i) in response to a radial compression force exerted thereon (for example, in the collapsed state of the valve on the holder), the holder has a first shape defining an exposed engagement region for engaging at least a portion of the prosthetic heart valve for restraining axial displacement of the prosthetic valve in at least one axial direction of the catheter, and (ii) in response to removal of the radial compression force (for example, upon expansion of the valve), at least a portion of the holder transitions to a second shape.

The second shape may be configured to permitting axial sliding of the holder with respect to the valve (e.g. not substantially restraining said axial displacement of the prosthetic valve and/or not presenting the exposed engagement region of the first shape).

The holder may comprise at least one element biased to define at least partly the second shape of the holder (e.g. corresponding to a deployed state of the at least one element). The at least one element may be transitioned (e.g. be collapsible) against the effect of the bias, to define at least partly the first shape (e.g. corresponding to a non-deployed state of the at least one element). The at least one member may define a cage-like profile on and/or around a holder hub carrying the engagement region.

The at least one element may exert a bias force on the prosthetic valve for separating the engagement region of the holder from the valve upon valve expansion.

The at least one element may be movable and/or deformable when transitioning from the non-deployed state to the deployed state. The at least one element may be transitioned reversibly between the two states In some embodiments, the at least one element may be biased to the deployed state, and be transitioned (e.g. be collapsible) to the non-deployed state against the effect of the bias. In some embodiments, the at least one element may be of or comprise one or more of: resilient material; elastic material; pseudo-elastic material; shape-memory material (for example shape-memory alloy).

(j) The same element or member may represent the aforementioned fender (if implemented), and/or the aforementioned separator (if implemented), and/or the aforementioned disengagement device (e.g. ejector) if implemented, and/or the aforementioned cage (if implemented), and/or the aforementioned at least one element (if implemented), and/or the aforementioned element defining a stop surface (if implemented).

In the preferred embodiment, a deployable cage-like element is carried on a body portion of the stent-holder. The cage-like element comprises a hub from which project plural fingers or elements. The fingers or elements slide (e.g. at least partly in an axial direction) in slots in the body portion of the stent-holder, to facilitate transition of the cage-like element between deployed and non-deployed positions.

(k) Additionally or alternatively to any of the above, a plurality of elements may be associated with the holder. The elements may be biased towards a radially outwardly deployed state, and collapsible under a radial compression force to a radially non-deployed state in which at least a portion of each element is moved to a position defining a smaller radial profile than in the deployed state.

In some embodiments, the elements are configured to be substantially non-interlocking with a said prosthetic valve. Additionally or alternatively, in some embodiments, the elements are configured not to restrain a said prosthetic valve with respect to the holder.

The number of elements may be at least three. Additionally or alternatively, the number of elements may equal or be greater than a number of engagement areas of the engagement region of the holder, each engagement area configured for engagement by an attachment element of a said prosthetic heart valve.

At least one of the elements may comprise an aperture in register with a male projection of the holder.

In some embodiments, the elements may extend axially across the engagement region, and may extend at least partly beyond the engagement region in both axial directions of the delivery catheter.

In some embodiments, at least in the deployed state, the elements may present a bulbous and/or ramp profile at the engagement region of the holder.

In some embodiments, at least some of the elements may be coupled to or integral with a common hub. The hub may optionally positioned axially to one side of the holder, the hub being in a region configured to be overlapped by a portion of a said prosthetic valve in use.

Additionally or alternatively to a hub, at least one end of at least some elements may be free ends (for example, in the sense of not being fixed to a hub). In some embodiments, the free ends are slidable in recesses of the holder. Additionally or alternatively, the holder may further comprise a cover for covering and/or constraining the free ends of the elements, at least in a certain direction of movement.

In some embodiments, the delivery catheter may further comprise a sheath translatable with respect to the holder between a first position in which the sheath surrounds at least a first portion of the holder, and a second position in which the sheath does not surround the first portion of the holder. In the deployed state the elements may define a profile that is larger radially than a mouth of the sheath that translates over the holder.

In some embodiments, the elements may be the same members providing the aforementioned fender (if implemented), and/or the aforementioned separator (if implemented), and/or the aforementioned disengagement device (e.g. ejector) if implemented, and/or the aforementioned cage (if implemented), and/or the aforementioned at least one element (if implemented), and/or the aforementioned element defining a stop surface (if implemented).

(I) The delivery catheter may comprise a valve-expansion control device for applying force to the prosthetic valve to control transitioning of the prosthetic valve from a collapsed condition for delivery, to expanded configuration for implantation. In some embodiments, the prosthetic valve may be self-expanding from the collapsed condition (and preferably to the expanded condition). The valve-expansion control device may comprise at least one sheath (optionally first and second sheaths) for surrounding at least a portion of the valve to constrain the valve in the collapsed condition. Translation of the at least one sheath out of constraining engagement with the prosthetic valve allows the prosthetic valve to self-expand. Alternatively, in some embodiments, the prosthetic valve may be non-self-expanding. The valve-expansion control device may comprise at least one forced expansion device (for example, an inflatable dilation balloon) for bearing on the valve to expand the prosthetic valve out of the collapsed condition.

(m) The delivery catheter may comprise a holder for engaging the valve in the collapsed state of the valve, a sheath translatable with respect to the holder between a first position in which the sheath surrounds at least a first portion of the holder, and a second position in which the sheath does not surround the first portion of the holder, the delivery catheter further comprising an interface member biased towards a radially expanded condition for (i) bridging a gap between the holder and the sheath when in the second position, and/or (ii) defining a generally smooth interface surface between the holder and the sheath when in the second position.

With such an arrangement, the interface member may reduce any risk that a portion of the valve could become hooked in a gap between the sheath and the holder, during withdrawal of the delivery catheter. The interface member may bridge the gap and/or define a generally smooth interface surface, either or both of which reduce risk of hooking. This may apply especially when the sheath is in the second position, but also when in the first position.

The interface member may be associated with the holder. For example, the interface member may form part of, or be carried by, or coupled to, the holder.

The interface member may be compressible to a radially collapsed condition in order to fit within the sheath when the sheath is in the first position. The interface member may expand to a radially expanded condition when the sheath is translated to the second position. The interface member may be reversibly deformable between the radially collapsed condition and the radially expandable condition.

The interface member may be of or comprise one or more of: resilient material; elastic material; pseudo-elastic material; shape-memory material (for example shape-memory alloy.

In some embodiments, the interface member comprises a cage structure (or cagelike structure). The cage structure may comprise plural deformable struts. The struts may be coupled at at least one end to a hub, optionally to two hubs at opposite ends.

The interface member may have a generally bulbous shape in the radially expanded condition, and a less bulbous shape (for example a more cylindrical shape whether or not exactly cylindrical) in the radially collapsed condition.

In some embodiments, the interface member may be integral with, or represented by the same element as the aforementioned fender (if implemented), and/or the aforementioned separator (if implemented), and/or the aforementioned disengagement device (e.g. ejector) if implemented, and/or the aforementioned cage (if implemented), and/or the aforementioned at least one element (if implemented), and/or the aforementioned element defining a stop surface (if implemented). Alternatively, the interface member may be a separate element.

Although explained above in terms of a delivery catheter, the ideas described in the present disclosure may be expressed alternatively in combination with a prosthetic valve, and/or as a holder for a delivery catheter, and/or a method of deployment.

Additional aspects are defined in the claims.

BRIEF DESCRIPTION OF THE DRAWINGS

Although various ideas, aspects and features are highlighted above and in the appended claims, protection is claimed for any novel feature or idea described herein and/or illustrated in the drawings whether or not emphasis has been placed thereon.

Non-limiting embodiments of the invention are now described with reference to the accompanying drawings, in which.

DETAILED DESCRIPTION

Figure 1:
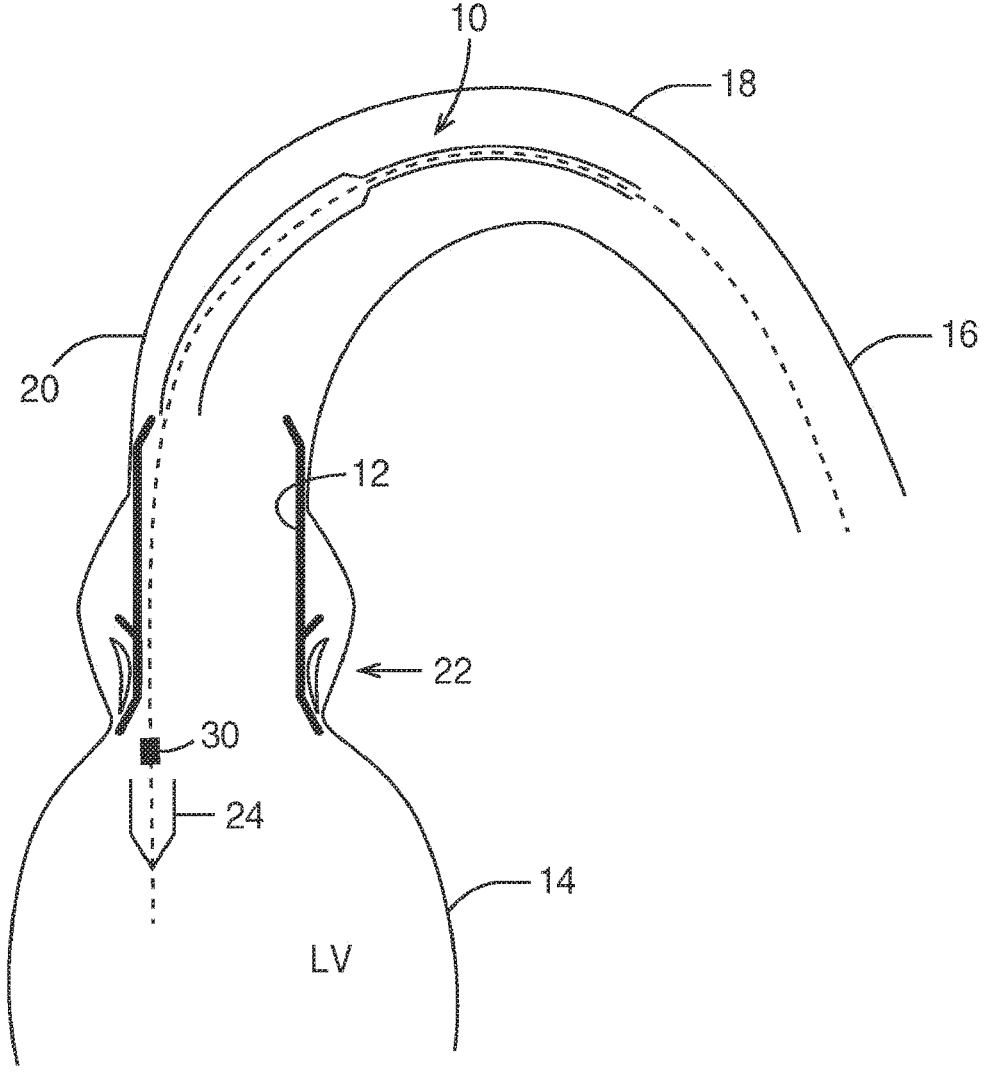
FIG. 1 is a schematic section illustrating implantation of a prosthetic stent-valve by a twin-sheath arterial delivery catheter.
Figure 2:
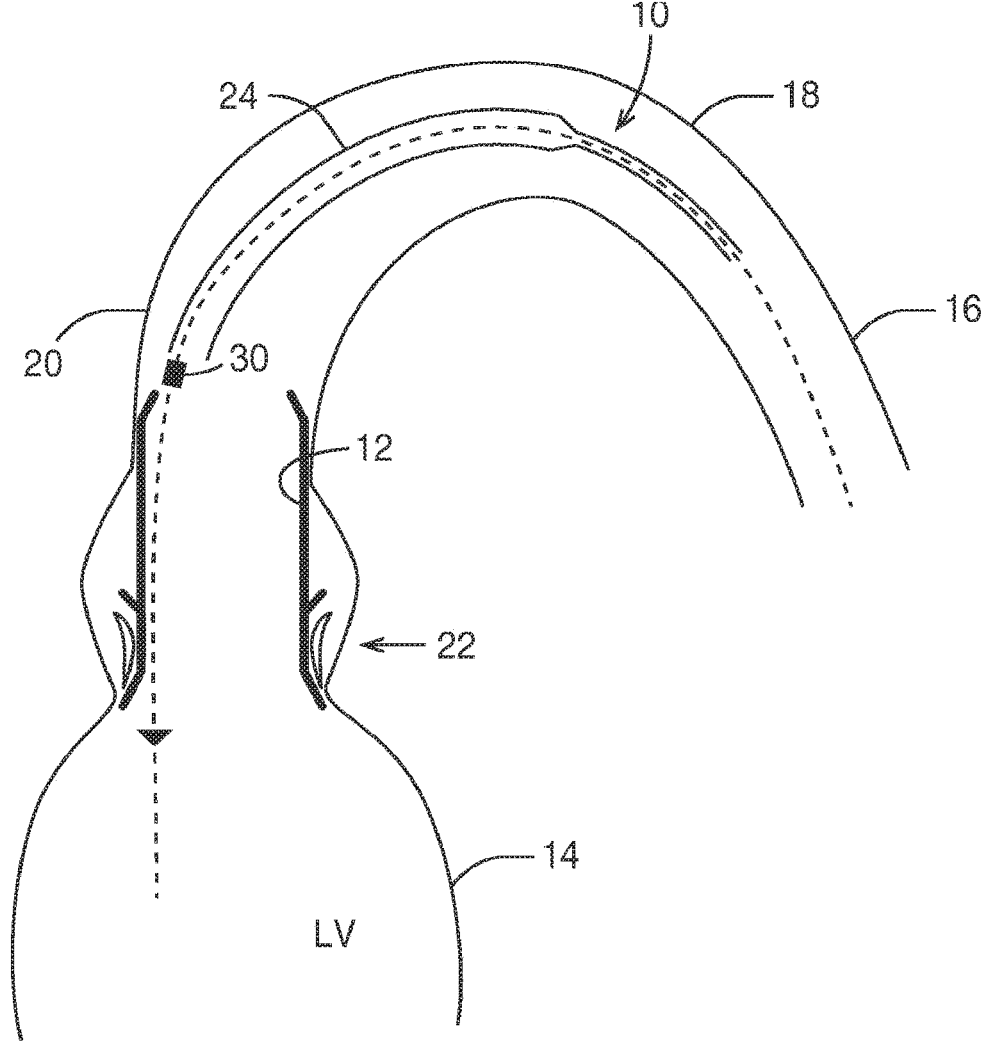
FIG. 2 is a schematic section similar to FIG. 1, but showing a single sheath delivery catheter.

Referring to FIGS. 1 and 2, a delivery catheter 10 is illustrated for delivery of a prosthetic cardiac valve 12 (e.g. a stent-valve) by an arterial approach to the heart 14. For example, the catheter 10 may be advanced through the descending aorta 16, around the aortic arch 18, and through the ascending aorta 20 to the aortic valve position 22 at the exit of the heart left ventricle LV.

The prosthetic valve 12 is configured to be expandable from a collapsed condition (not shown) for delivery, to an expanded condition (as shown in FIGS. 1 and 2) for implantation. The valve 12 may comprise a stent component supporting a valvular structure. In the illustrated embodiments, the valve 12 is a self-expanding type valve that can be restrained in the collapsed condition by means of one or more sheaths 24 of the delivery catheter 10. When the one or more sheaths 24 are translated out of surrounding engagement with the valve 12, the valve 12 becomes free to self-expand at the implantation site. In other embodiments, the valve 12 could be plastically expandable, and retained in collapsed form by its own internal strength when compressed (e.g. crimped).

More detail of an example valve 12 may be found it the aforementioned WO-A-2012032187 to which the reader is referred. Other constructions and geometries of expandable prosthetic valve 12 may be used as known in the art. An example of a valve (e.g. stent-valve) 12 is also described later with reference to FIGS. 12-14

FIG. 1 illustrates an example of a delivery catheter 10 having first and second constraining/deployment sheaths 24 for controlling the expansion of the valve 12. The sheaths 24 are translated in a controlled sequence for progressively releasing portions of the valve 12. The released portions of the valve self-expand in place.

More detail of an example delivery catheter 12 having twin sheaths may be found in the aforementioned WO 2012038550 to which the reader is referred. More details may also be described later below with reference to FIGS. 9-11. FIG. 2 illustrates an alternative example of delivery catheter 12 having a single sheath 24 that is retracted in a direction away from the heart 14, to cause the valve 12 to expand progressively from bottom to top (in the schematic orientation of the drawing).

The delivery catheter 12 (in either example) may comprise a holder 30 having an engagement region 32 for restraining displacement of the valve 12 in at least one axial direction of the catheter 10, while at least a portion of the valve 12 is restrained in the collapsed condition around the holder 30. The holder 30 is useful to prevent the prosthetic valve 12 from jumping free of the delivery catheter 10 prematurely (for example, when only a small portion of the valve 12 remains constrained by the sheath 24). Premature jumping free may result in malpositioning of the valve 12, and subsequent inability to reposition and/or recapture the valve 12 by the delivery catheter 10. The holder 30 (or at least the engagement region 32) may be configured with a male and/or female engagement region 32, and/or an annular flange or wall, in order to mate with the valve 12 when in the collapsed state. For example, the engagement region may comprise one or more projections, apertures or recesses that mate with complementary attachment elements (e.g. apertures or projections) of the valve 12. Expansion of the valve 12 moves the attachment elements to a wider radius than those of the holder, the intention being that the stent-valve 12 can release from the holder 30 upon expansion of the valve 12. An example of valve and attachments is described in more detail later. The valve may, for example, have two, three, four, or more attachment elements. The engagement region 32 of the holder 30 may have a corresponding number of engagement areas (for example, matching the number of attachment elements of the valve 12).

The position of the holder 30 may vary according to the design of the valve 12 and/or the delivery catheter 10. In the example of FIG. 1, the holder 30 is positioned at an operator-distal (heart-proximal) portion of a valve containment region of the delivery catheter, such that the holder 30 is directly adjacent to the heart 14. In the example of FIG. 2, the holder 30 is positioned at an operator-proximal (heart-distal) portion of a valve containment region of the delivery catheter, such that the holder 30 is positioned in the ascending aorta.

As illustrated in both FIGS. 1 and 2, the delivery catheter 10 can tend to be placed or pressed (as a result of passing around the aortic arch 18), against a wall of the ascending aorta 20, and or the native valve site 22. It has been appreciated that in some cases (depending on the patient's individual anatomy, for example), such positioning can result in the holder 30 remaining engaged to a portion of the valve 12. Alternatively, there may be a risk of the holder 30 hooking a portion of the valve 12 during removal of the delivery catheter. It is believed that such engagement may explain at least some of the non-rare cases of valve dislodgement referred to in the introduction herein.

In some embodiments, the delivery catheter 10 (and optionally the holder 30) is configured to mitigate such issues.

Figure 3:
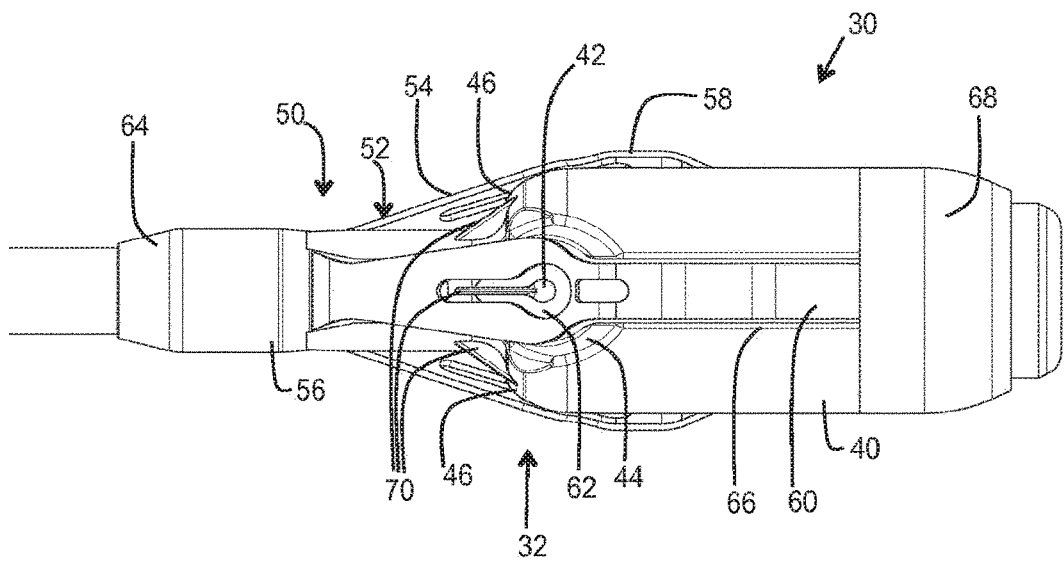
FIG. 3 is a schematic side view of a first example of stent holder of FIG. 1 in isolation in a first angular orientation.
Figure 4:
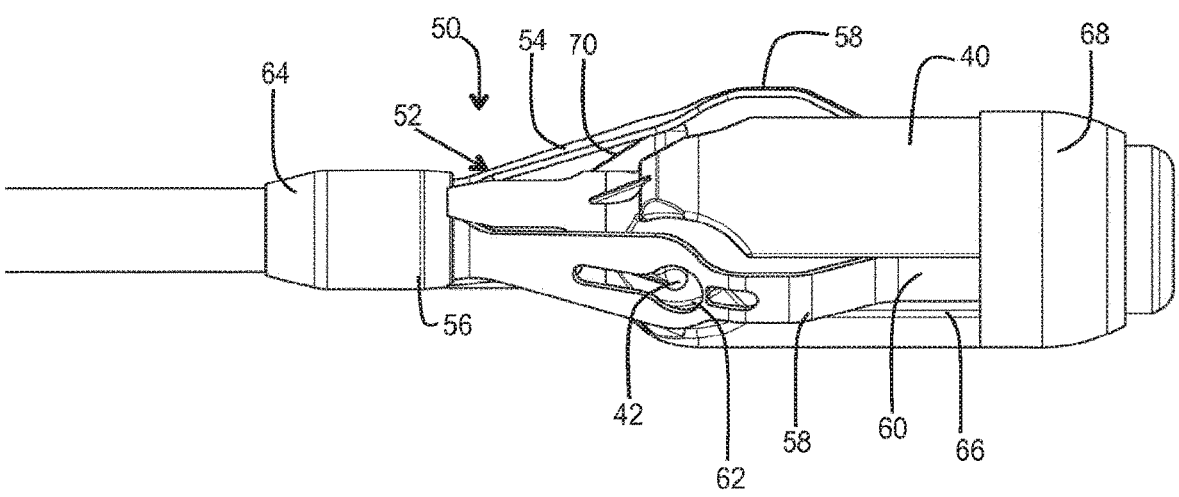
FIG. 4 is a schematic side view of the stent holder of FIG. 3 in a second angular orientation.
Figure 5:
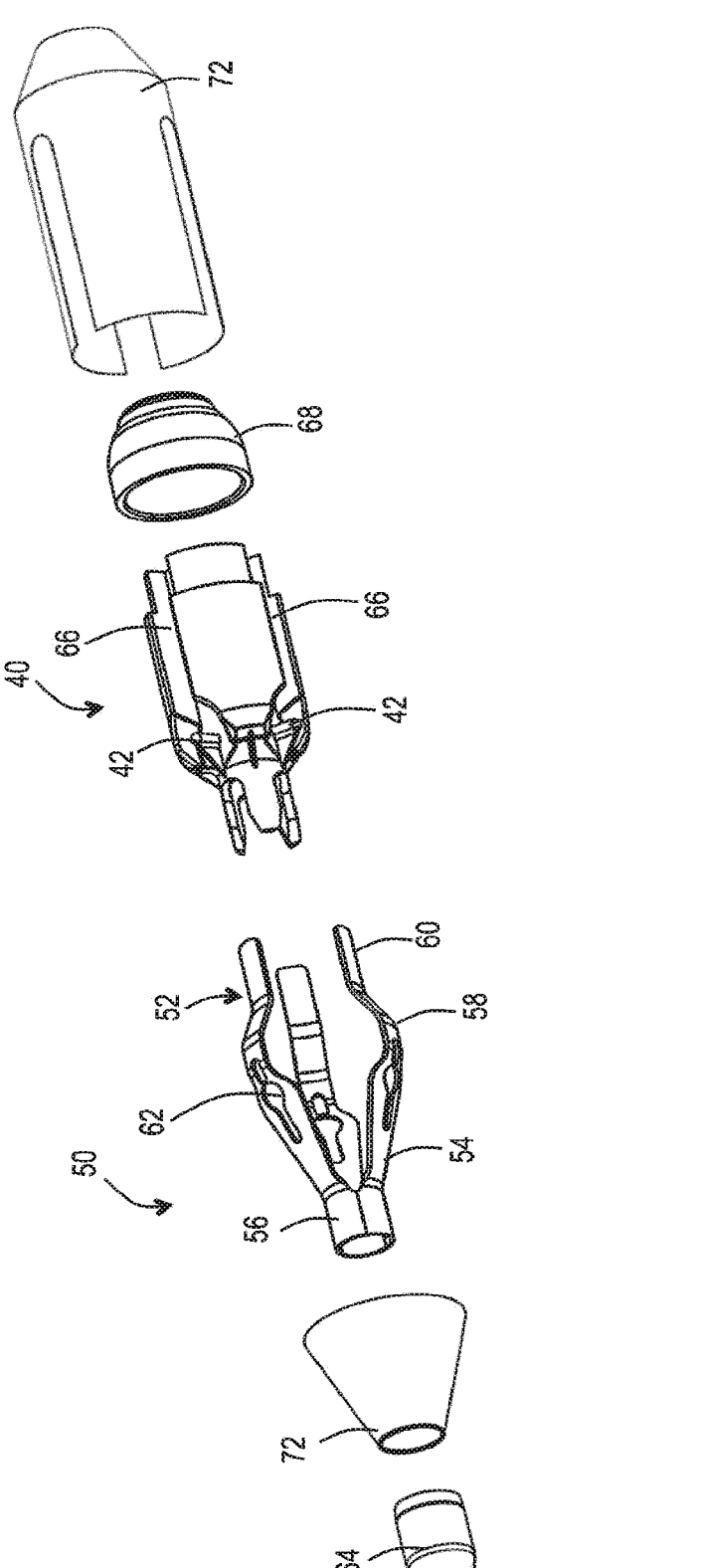
FIG. 5 is a schematic exploded view of the stent holder of FIGS. 3 and 4.

Referring to FIGS. 3-5, the stent holder 30 may comprise a body 40 including an engagement region 32. The engagement region 32 may be defined by one or a combination of any two or more of: projections 42; recesses 44; abutment wall 46.

A multi-limbed device 50 may be provided, optionally as part of the holder 30 or associated therewith. In some embodiments, the multi-limbed device 50 is biased to a deployed state (as shown in the drawings), in which the device can act as a fender (aforementioned aspect (b)), and/or a separator (aforementioned aspect (c)), and/or a disengagement device (e.g. ejector) (aforementioned aspect (d), and/or a cage (aforementioned aspect (e), and/or at least one biased element (aforementioned aspect (f)), and/or an element defining a stop surface (aforementioned aspect (g)), and/or a deployable ramp (aforementioned aspect (h)), and/or an element for changing the effective shape of the holder (aforementioned element (i)). The device 50 may be collapsible against the effect of the bias to a non-deployed state (not shown). For example, in the non-deployed state, the device 50 may be accommodated substantially flat against and/or at least partly within the profile of, the body 40.

In some embodiments, the device 50 may be of or comprise one or more of: resilient material; elastic material; pseudo-elastic material; shape-memory material (for example shape-memory alloy).

The multi-limbed device 50 may comprise resiliently deformable limbs, fingers or elements 52. The deployed shape of each element 52 may be selected as desired. In the illustrated form, each element 52 generally comprises a ramp portion 54 that diverges from a hub 56 of the device 50, an apex 58 (e.g. defining a bulge shape), and a free end portion 60.

In some embodiments, the elements 52 are configured to be substantially non-interlocking with a said prosthetic valve. Additionally or alternatively, in some embodiments, the elements 52 are configured not to restrain a said prosthetic valve with respect to the holder.

The number of elements 52 may optionally be at least three. Additionally or alternatively, the number of elements 52 equals or is greater than the number of engagement areas of the engagement region 32 of the holder 30.

The elements 52 may extend axially across the engagement region 32, and extend at least partly beyond the engagement region 32 in both axial directions of the delivery catheter. As may be described later, the hub 56 may be in a region configured to be overlapped by a portion of a said prosthetic valve in use.

At least some of the elements 52 may include an aperture 62 through which the projection 42 of the holder can project. The hub 56 may be fixedly attached to the body 40 by means of a fixation sleeve 64. The free end portions 60 may slide (e.g. at least partly in an axial direction) in recesses 66 (e.g. elongate slots or grooves) of the body 40 in which the free end portions 60 are received. A cover (e.g. cap) 68 constrains the free end portions 66 captive, yet freely slidable in the recess 66. The cover 68 also prevents any risk of the free ends of the elements 52 causing damage to the valve 12 or to the native anatomy. Such risk might otherwise be present were free ends of a relatively thin element to be left exposed.

The sliding movement of the end portions 60 permits the elements to elongate when transitioning to the non-deployed state. For example, when a valve 12 is loaded into or onto the delivery catheter 10 and collapsed around the holder 30, the radial compression force against the holder may cause the elements 52 to collapse to their non-deployed state. In the non-deployed state, the elements 52 do not obstruct substantially, or obscure substantially, the function of the engagement region 32. For example, the elements 52 are pressed radially inwardly, such that the projections 42 project through the apertures 62, to engage the valve 12.

Upon subsequent expansion of the valve 12, the elements 52 are biased to transition to their deployed states, as illustrated in FIGS. 3-5. For example, the elements 52 may bear outwardly against the valve 12 in order to urge the engagement region 32 of the holder 30 separate from the valve and/or eject the valve 12 clear of the engagement region 32. The elements 52 may act as a fender to urge the engagement region away from subsequent engagement with the valve 12. The elements 52 may substantially reduce (or completely reduce) the projection height of the projections. The elements 52 may change the outward shape or profile of the holder 30 to a shape that permits sliding contact with the valve 12 without re-engagement or hooking of the valve by the engagement region 32. The elements 52 may define a cage-like shroud over the engagement region 32. The elements 52 may deploy a ramp portion 52 that permits sliding contact, or acts as a guide to ramp the holder 30 over portions of the valve 12 that the holder 30 might otherwise be capable of hooking.

Figure 6:
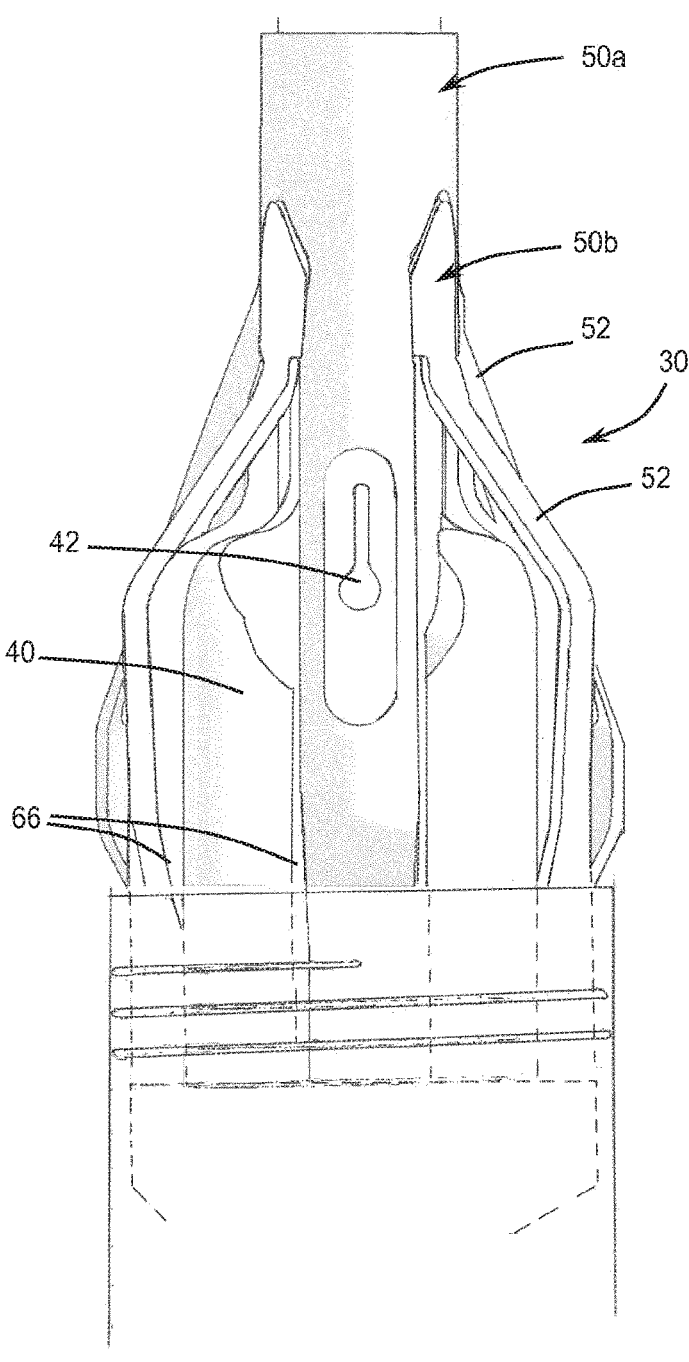
FIG. 6 is a schematic side view of a second example of stent holder.
Figure 7:
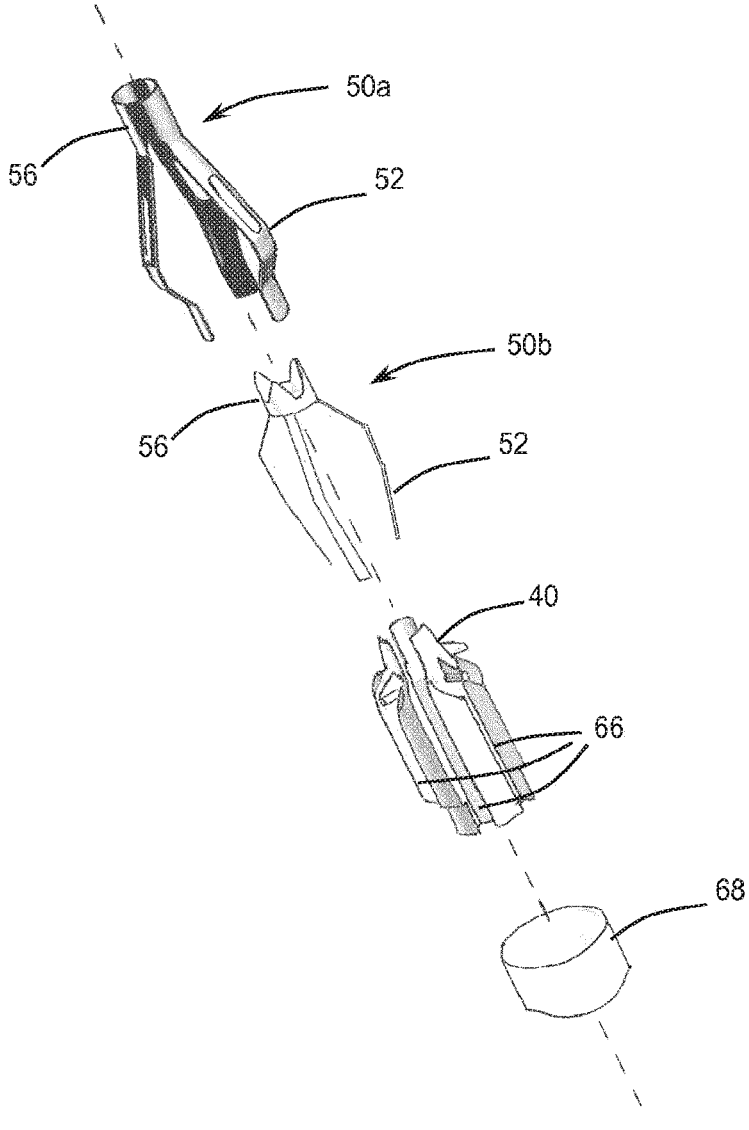
FIG. 7 is a schematic exploded view of the stent holder of FIG. 6.

FIGS. 6 and 7 illustrate a further example comprising plural multi-limbed members 50a and 50b that are angularly offset with respect to each other. Such an arrangement can enable a greater number of elements 52 to be accommodated within the very confined space available around each hub 56. For example, if each device 50 may comprise three elements 52, the combination of two devices 50a, 50b may collectively provide a cage-like structure of six elements 52. The body of the holder 30 may comprise a corresponding number of accommodation recesses 66, for example, one for each element 52. The hubs 56 may have a keyed fit with respect to each other.

In all examples, the engagement portion 32 of the holder 30 may further include ramp sections 70 for additional ramping effect to avoid unintended re-engagement or hooking of the valve 12. Additionally or alternatively, the holder 30 may comprise one or more protective and/or friction-reducing flexible skirts or petals 72 to facilitate use of the catheter 10 and loading of a valve 12. The skirts or petals 72 may be illustrated for example in FIG. 5, but may be omitted in other drawings to avoid obscuring other detail.

Figure 8:
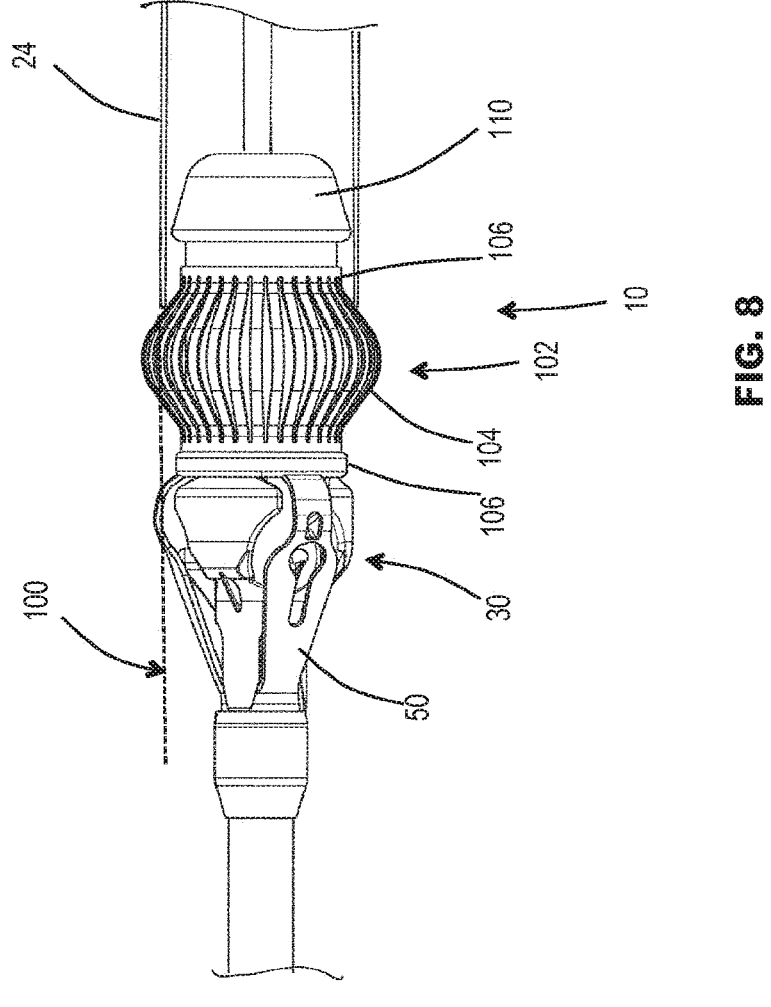
FIG. 8 is a schematic side view of a distal end of a delivery catheter with a further example of stent holder.

Referring to FIG. 8, a distal end portion of a further embodiment of delivery catheter 10 is illustrated. The delivery catheter 10 comprises a stent holder 30, which may optionally be similar to any of the holders 30 described above, and include any of the examples of multi-limbed device 50 described above.

The delivery catheter 10 further comprises at least one constraining sheath 24. The constraining sheath 24 is axially translatable between a first position (indicated by the arrow 100) in which the constraining sheath 24 surrounds at least a portion (and optionally the majority or substantially all) of the stent holder 30, and a second position (as illustrated in FIG. 8) in which the constraining sheath 24 does not surround the portion of the stent holder 30. In some embodiments, the sheath 24 may translate in a distal direction of the delivery catheter, when moving from the first position to the second position. The sheath 24 may be a unique sheath of the delivery catheter 10, or it may be one (e.g. a distal sheath) of a multiple sheath (e.g. dual sheath) delivery catheter, for example, as described in the aforementioned WO-A-2012032187, and in the example further below.

The delivery catheter 10 further comprises an interface member 102. The interface member 102 may be associated with the stent holder 30. In some embodiments, the interface member 102 is carried by, or forms part of, the stent holder 30.

The interface member 102 may be biased towards a radially expanded condition, as illustrated in FIG. 8. In the radially expanded condition, the interface member 102 may serve to (i) bridge a gap between the holder 30 and the sheath 24 when in the second position, and/or (ii) defining a generally smooth interface surface between the holder 30 and the sheath 24 when in the second position.

With such an arrangement, the interface member 102 may reduce any risk that a portion of the valve could become hooked in a gap between the sheath and the holder, during withdrawal of the delivery catheter after implantation of the prosthetic valve. The interface member 102 may bridge the gap and/or define a generally smooth interface surface, either or both of which reduce risk of hooking. This may apply especially when the sheath 24 is in the second position, but also when in the first position.

The interface member 102 may be compressible to a radially collapsed condition (not shown) in order to fit within the sheath 24 when the sheath 24 is in the first position. The interface member 102 may expand to the radially expanded condition when the sheath 24 is translated to the second position. The interface member 102 may be reversibly deformable between the radially collapsed condition and the radially expandable condition.

The interface member may be of or comprise one or more of: resilient material; elastic material; pseudo-elastic material; shape-memory material (for example shape-memory alloy. An example shape-memory alloy is nitinol.

In some embodiments, the interface member 102 comprises a cage structure (or cage-like structure). The cage structure may comprise plural deformable struts 104. The struts may be coupled at at least one end to a hub 106, optionally to two hubs 106 at opposite ends in the form illustrated in FIG. 8.

The interface member 102 may have a generally bulbous shape in the radially expanded condition (as illustrated in FIG. 8), and a more cylindrical shape (even if not exactly cylindrical) in the radially collapsed condition (not shown).

In some embodiments, the interface member 102 may be integral with the multi-limbed device 50. For example, the interface member 50 may be an extension of the multi-limbed device 50. Optionally, the interface member 102 may move to the radially expanded condition at the same time as deployment of the multi-limbed device 50. In the form illustrated in FIG. 8, the interface member 102 is distinct from the multi-limbed device 50. The tips of the limbs of the multi-limbed device 50 may be received within one hub 106. The other hub 106 may be capable of sliding axially in order to accommodate axial elongation of the interface member 102 when in the radially collapsed condition, but be retained by an axial stop 110 of the stent holder body.

Figure 9:
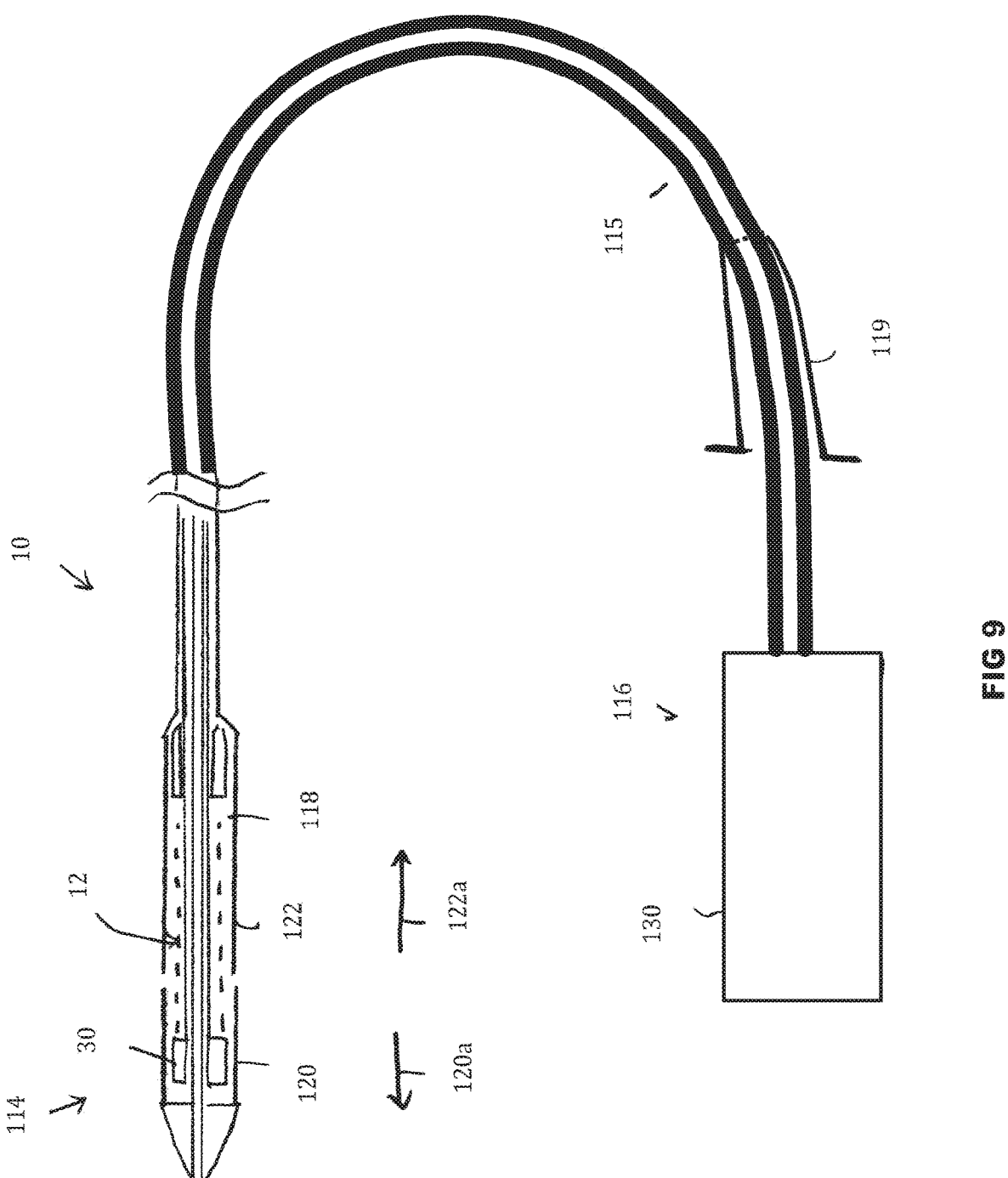
FIG. 9 is a schematic view of an example delivery catheter with sheaths in a closed state.
Figure 10:
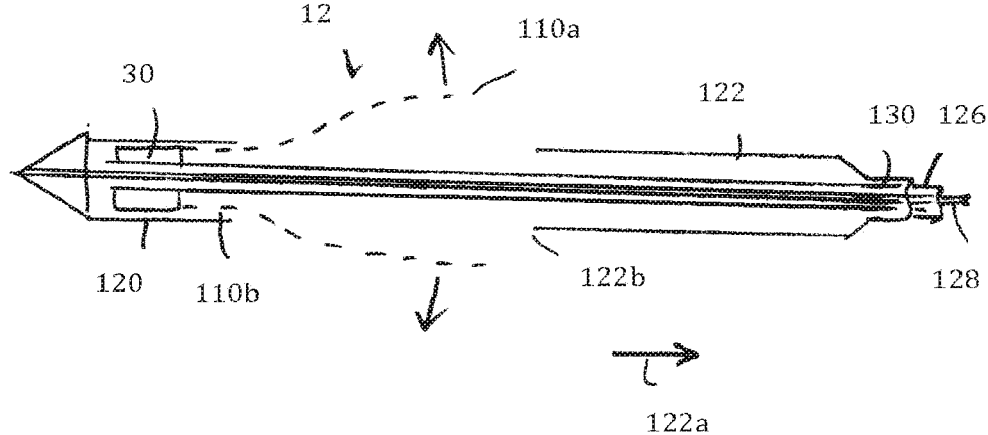
FIG. 10 is a schematic view showing the distal end of the delivery catheter of FIG. 9 with one sheath open.
Figure 11:
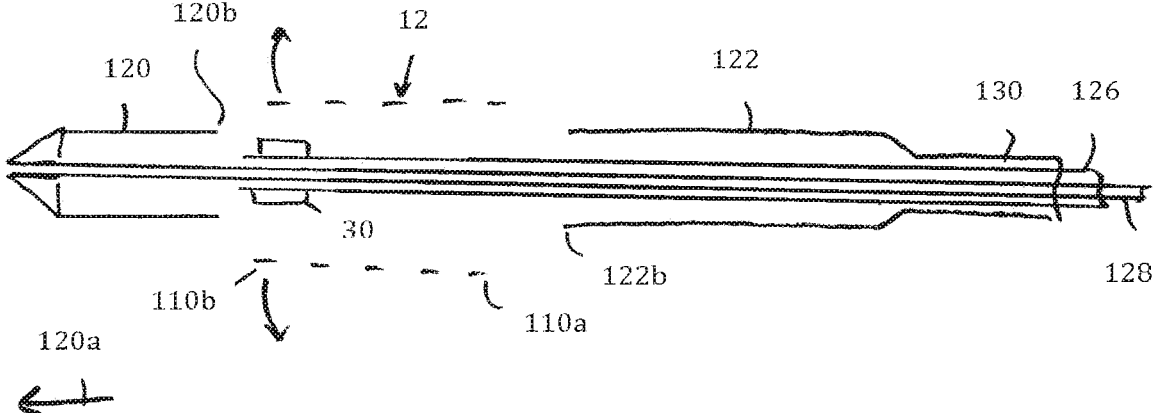
FIG. 11 is a schematic view showing the distal end of the delivery catheter of FIG. 9 with both sheaths open.

Referring to FIGS. 9-11, an example delivery catheter incorporating any of the holders 30 described above is now described more completely, by way of information only. The delivery catheter is not limited to the following construction, although additional advantages may derive from using the holder 30 in the following construction of delivery catheter.

Referring to FIGS. 9-12, a stent-valve 12 and a delivery catheter 10 therefor are illustrated in isolation. The delivery catheter 10 may have a distal portion 114 towards one end for insertion into a patient's anatomy, and a proximal portion 116 towards an opposite end from which the delivery catheter is manipulated in use by an operator. A barrel or stem portion 115 may extend between the distal and proximal portions.

As used herein, the terms "distal" and "proximal" for the delivery catheter may refer to relative position with respect to an operator.

The distal portion 114 of the catheter 112 may comprise an accommodation region 118 for accommodating the stent-valve 12 in a collapsed form for introduction into the anatomy. The stent-valve 12 may be a cardiac stent-valve. The delivery catheter 10 may be configured to permit delivery of the stent-valve 12 to, and deployment at, a desired site of implantation while the heart remains beating, for example, using a minimally invasive surgical and/or percutaneous procedure. In some embodiments, the catheter 10 may be configured for introduction into the anatomical vascular system, and for advancement along the vasculature system to the desired site of implantation. For example, the catheter 10 may be configured for introduction into the femoral artery, and guided retrograde via the descending aorta, aortic arch, and ascending aorta to the heart (sometimes called a transfemoral access). The catheter 10 may have a length of at least about 1 m to provide sufficient length insertable into the anatomy. In other embodiments, the catheter 10 may be insertable via the subclavian artery and guided retrograde to the heart (sometimes called transubclavian access). In other embodiments, the catheter may be insertable via the ascending aorta (sometimes called transaortic access). In other embodiments, the catheter 10 may be inserted directly into a chamber of the heart such as a ventricle (for example, left ventricle) via a direct access route while the heart remains beating. For example, a direct access route may be through an aperture opened in the apex of the heart (sometimes called a transapical access).

The size of access aperture into the anatomy may depend on the outer diameter of the distal portion 114. The barrel portion 115 may be slightly smaller than, or the same diameter as, the distal portion 114 as desired. For minimally invasive surgery, it is desired that the access aperture into the anatomy be as small as practical, bearing in mind the size to which the stent-valve 12 can be collapsed without risk of damage. An introducer 119, for example, a standard arterial introducer, may optionally be used at the access aperture into the anatomy. The optional introducer 119 may have a size of 20 French or smaller, for example, 18 French or smaller. The distal portion 114 may be dimensioned for insertion through such a size of introducer 119.

The stent-valve 12 may be expandable from a compressed or collapsed condition to a functional and/or expanded condition, in order to anchor the stent-valve 12 at the implantation site. For example, the stent-valve 12 may form a friction and/or interference fit with respect to the native anatomy. Various shapes and geometries of stent-valve 12 may be used to fit the anatomy at the site of implantation. A generally cylindrical stent-valve 12 is illustrated here for clarity, but the invention is not limited to a cylindrical shape, and may be especially advantageous with non-cylindrical shaped stent-valves 10. A more detailed example of stent-valve 12 is described later, and all details of the delivery catheter 10 are explicitly applicable to the stent-valve shape described later.

The stent-valve 12 may be self-expanding and/or may be configured to be expandable by swelling of an expander (for example, a balloon not shown). Self-expanding stent-valves 12 may be constructed from, or use, shape-memory material, for example a shape-memory metal alloy (such as nitinol). A self-expanding stent-valve 10 may be retained in its compressed state by being constrained within a sheath 120/122 of the delivery catheter 10. Upon at least partial release from the sheath 120/122, the released portion of the stent-valve 12 may be free to expand. Non-self-expanding stent-valves 10 may also be made of shape-memory material, or from stainless steel, or cobalt-chromium alloy. A non-self-expanding stent-valve 12 may also be contained at least partly within a sheath 120/122 to protect the stent-valve 12 and/or facilitate smooth introduction through the anatomy.

The distal portion 114 of the catheter 10 may comprise at least one sheath 120 and/or 122 that is translatable between a closed position at least partly covering the accommodation region 118 and/or the stent-valve 12 therein, and an open position at least partly opening or exposing the accommodation region 118 and/or at stent-valve 12 therein. In the present example, the catheter comprises two sheaths 120 and 122, both shown in their respective closed positions in FIG. 9 to at least partly (optionally substantially entirely) cover the stent-valve 12 in the accommodation region 118. The sheaths 120 and 122 may be translatable in opposite directions to respective open positions. A first (e.g. more distal) of the sheaths 120 may be translatable in a distal direction (indicated by arrow 120a in FIG. 9) to an open position (FIG. 11). The first sheath 120 may also be referred to as the distal sheath. A second (e.g. more proximal) of the sheaths 122 may be translatable in a proximal direction (indicated by arrow 122a in FIG. 9) to an open position (FIGS. 10 and 11). The second sheath 122 may also be referred to as the proximal sheath. Use of first and second opposed sheaths 120 and 122 may provide good versatility for release of the stent-valve 10 from the accommodation region. For example, referring to FIG. 10, by translating the second sheath 122 to or towards its open position without translating the first sheath 120, a portion 110a of the stent-valve 12 previously covered by the second sheath 122 may be released (at least partly) before a portion 110b of the stent-valve 12 covered by the first sheath 120. The portion 110b may be released subsequently by translation of the first sheath 120 to or towards its open position (FIG. 11). The length of the second sheath 122 may be greater than the length of the first sheath 120. For example, the ratio of the second sheath length divided by the first sheath length may be at least 1.1, optionally at least 1.2, optionally at least 1.3, optionally at least 1.4, optionally at least 1.5, optionally at least 1.6, optionally at least 1.7, optionally at least 1.8, optionally at least 1.9, optionally at least 2.0, optionally at least 2.1, optionally at least 2.2, optionally at least 2.3, optionally at least 2.4, optionally at least 2.5, optionally at least 2.6, optionally at least 2.7, optionally at least 2.8, optionally at least 2.9, optionally at least 3, optionally at least 3.5, optionally at least 4 or optionally at least 4.5, or optionally at least 5. Use of a relatively short first sheath 120 may reduce risk of trauma in use. The first sheath 120 advances distally along a path that may be less controlled than the second sheath that benefits from a more controlled path defined by the path adopted by the barrel portion 115 of the catheter. For example, in the case of transvascular access (e.g. transfemoral access), the first sheath 120 may advance into the ventricle of the heart. Use of a relatively short first sheath 120 may reduce the degree to which the catheter 10 has to penetrate into the ventricle, and risk interfering with delicate tissue surfaces. In the case of direct access (e.g. transapical access), the first sheath 120 may advance into the ascending aorta. Use of a relatively short first sheath 120 may reduce the degree to which the first sheath 120 has to penetrate the space of the ascending aorta, and risk interfering with the aorta wall.

One or both of the sheaths 120 and 122 may be of plastics optionally including reinforcement to resist radial expansion of the sheath. One suitable plastics is a poly ether block amide (PEBA), for example PEBAX™. Reinforcement may be provided by a helical coil embedded within the sheath. The helical coil may be of metal, for example, stainless steel filament.

The sheaths 120 and 122 may have the same inner and/or outer diameter. The sheaths 120 and 122 may be configured not to overlap each other. Avoiding an overlap can avoid excess diameter of the distal portion that might otherwise be caused by the sheath walls overlapping each other.

The sheaths 120 and 122 may be capable of being positioned such that the sheaths 120 and 122 meet substantially end to end. Alternatively, the sheaths 120 and 122 may be configured such that the sheaths 120 and 122 remain spaced from each other, even in mutually closed positions of the first and second sheaths 20 and 22 when restraining a stent valve 12 ready for introduction into the body. For example, the minimum spacing may be at least 1 mm, or at least 2 mm, or at least 3 mm, or at least 4 mm, or at least 5 mm, or at least 6 mm. Additionally or alternatively, the spacing may be less than 10 mm, or less than 9 mm, or less than 8 mm, or less than 7 mm, or less than 6 mm, or less than 5 mm. In one form, the spacing is between about 4 mm and about 6 mm.

During the translations of the sheaths 120 and 122 the stent-holder 30 may retain the stent-valve 12 axially in position and/or restrain the stent-valve 12 against axial movement. The stent-holder 30 is represented purely schematically in FIGS. 9-11, and may corresponds to any of the holder examples described hereinbefore. The stent-holder 30 may prevent and/or obstruct any tendency of the stent-valve 12 to be dragged by translation of a sheath 120 or 122. Additionally or alternatively, the stent-holder 30 may prevent and/or obstruct any tendency for a self-expanding stent-valve 12 to jump free of the catheter if only a small portion of the stent-valve 12 remains constrained by the sheath 120 or 122. The stent holder 30 may be positioned in the accommodation region 118 at a position appropriate to engage the stent-valve 12 until final release of the stent-valve 12 from the accommodation region. In the illustrated example, a distal portion of the stent-valve 12 may be intended to be released last, and the stent-holder 30 may be positioned towards the distal end of the accommodation region 118. In other embodiments, if the proximal portion of the stent-valve 12 is intended to be released last, the stent-holder 30 could instead be positioned towards the proximal end of the accommodation region 118.

The delivery catheter 10 may further comprise, at its proximal end, a control handle 130 including one or more actuators for manipulating the one or more sheaths 120/122. For example, the actuators may generate relative axial movement which is transmitted to the sheaths via one or more nested tubes or shafts within the barrel.

Figures 12, 13, 14:
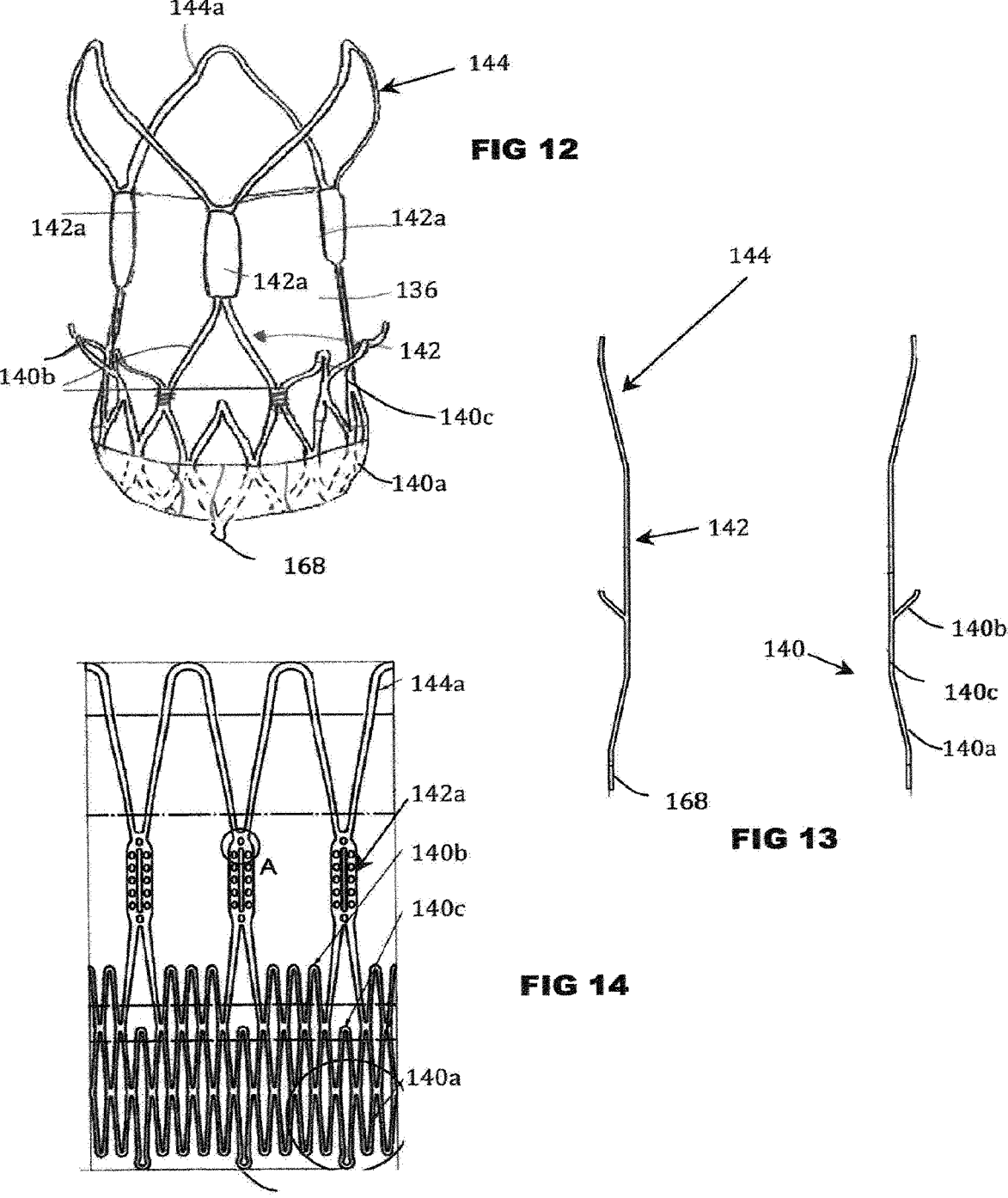
FIG. 12 is a schematic side view of an example expandable stent-valve.
FIG. 13 is a schematic section through a stent component of the valve of FIG. 12.
FIG. 14 is a schematic side view showing, in a single flat or "unrolled" plane, a detail of the stent component.

FIGS. 12, 13 and 14 illustrate a detailed example of a stent-valve 12 for which the delivery catheter 10 of any of the preceding embodiments may be eminently suitable. The disclosure in not limited to the illustrated example of stent-valve, although additional advantages may follow from using the illustrated example.

The stent-valve 12 may be of a self-expanding type that is resiliently biased towards the expanded and/or functional state, and is compressible to a compressed state by application of suitable radial compression forces. The stent-valve 12 remains in its compressed state while constrained. When the constraint is removed, the stent-valve 12 self expands towards the expanded and/or functional state. Alternatively, the stent-valve 12 may be of a non-self-expanding type that requires application of an expansion force to transform the stent-valve 12 from the compressed state to the expanded state.

The stent-valve 12 may comprise a stent component 134 supporting a plurality of valve leaflets 136. The leaflets 136 may collectively be referred to as a valve component, whether or not the leaflets 136 form an integral unit. The stent component 134 may provide an anchoring function for anchoring the stent-valve in the native anatomy and/or a support function for supporting the valve leaflets 136. The stent component 134 may be of any suitable material or materials. The stent component 14 may be of metal. Example materials include shape memory and/or superelastic alloys (for example, nitinol), stainless steel, or cobalt-chromium alloy. In the illustrated form, the stent component 134 is self-expanding and is of shape memory/superelastic alloy (e.g. nitinol). However, the stent component 134 could also be substantially non-self expanding.

The stent component 134 may have any profile desired for anchoring and/or aligning the stent-valve 12 with respect to the native anatomy at the desired implantation site. In some embodiments, the stent component 134 may be generally cylindrical in shape, or comprise one more generally cylindrical portions or portions lying on a generally cylindrical surface (e.g. 140c and 142a). Additionally or alternatively, the stent component 134 may be generally non-cylindrical in shape or comprise one or more generally non-cylindrical portions or portions lying on a non-cylindrical surface (e.g. 140a, 140b, and 144). Additionally or alternatively, the stent component 134 may comprise one or more anchor projections, and/or one or more stabilization portions.

Viewed in one aspect, the stent component 134 optionally has an inflow end and an outflow end, optionally is self-expandable from a compressed state for delivery towards a functional state upon implantation, the stent component 134 comprising an outflow structure, for example, in the form of a plurality of arches 144a at the outflow end each having an apex at the outflow end, the stent component further comprising a crown (e.g. superior crown) 140b intermediate the inflow and outflow ends, the crown 140b having a free extremity intermediate the inflow and outflow ends and directed towards the outflow end, and the stent-component further comprising a fixation section (e.g. inferior crown) 140a between the crown and the inflow end.

Additionally or alternatively, the stent component 134 optionally comprises an anchoring portion 140 defined, for example, by an inferior crown 140a and a superior crown (or other fixation section) 140b that together define a groove and/or waist 140c therebetween. The anchoring portion 140 may have a first resistance to compression, and may comprise a cellular lattice.

The stent component 134 optionally (further) comprises a valve support portion 142 comprising, for example, a plurality (e.g. three) commissural support posts 142*a*. The commissural support posts 142*a* may be arranged on a pitch circle diameter smaller than an extremity of at least one of the crowns 140*a* and 140*b*. The commissural support posts 142*a* may be arranged on a pitch circle diameter corresponding to the waist 140*c*. The commissural support posts 142*a* may partly overlap at least one of the crowns 140 and 142 in the axial direction, and extend axially beyond that respective crown. The commissural support posts 142*a* may be frame-like. The commissural support posts 142*a* may have a shape that follows, at least approximately, a peripheral contour of the valve, at least in the region of the valve periphery adjacent to the commissural support posts.

The stent component 134 optionally (further) comprises a stabilization or alignment portion 144 which may represent an outflow structure. The portion 144 may be defined, for example, by a plurality (e.g. three) wings or arches 144*a*. The arches 144*a* may extend from tips of the commissural support posts 142*a*, to define a vaulted structure thereover. The alignment portion 144 may have a greater flexibility than the anchoring portion 140 and/or the valve support portion 142. The alignment portion 144 may have a second resistance to compression that is smaller than the first resistance to compression of the anchoring portion 140. The alignment portion 144 may be less rigid (e.g. radially) than the anchoring portion 140 and/or the valve support portion 142.

The stent component 134 optionally (further) comprises an attachment element 68 for attaching the stent component 134 to the stent holder 30 of the delivery catheter 10. In the present embodiment, the attachment portion 68 is defined by a plurality (e.g. three) of extensions of cells of the inferior crown 140*a*, and have a shape corresponding to a completely or partly enclosed attachment eyes.

The valve component or leaflets 136 may be of any suitable natural and/or synthetic material(s). For example, the valve component/leaflets 136 may comprise porcine and/or bovine pericardium and/or harvested natural valve material. The leaflets may be supported to coapt or collapse to a closed position to obstruct flow in one direction therepast, while flexing apart to an open position to allow flow in an opposite direction. The valve component/leaflets 136 may be accommodated at the valve support portion 142 and/or at least partly within the anchoring portion 140. The leaflets may have side tabs. The tabs of adjacent pairs of leaflets may pass in pairs through slots in the support posts 142, be folded back and sutured on either side of the slot. The support posts 142*a* may have lines of suture holes either side of the slot to accommodate the sutures. Further suture holes may be provided above and/or below the slots. If desired the suture hole above the slot (indicated at A in FIG. 14) and/or the suture hole below the slot, may be omitted to save space.

The stent-valve 12 (e.g. the valve component 136) may further comprise an inner skirt and/or an outer skirt covering at least partly a respective inner or outer surface portion of the stent component 134. For example, the skirt(s) may cover at least a portion of the anchoring portion 140 and/or at least a portion of the valve support portion 142. The skirt(s) may be made of any suitable material, including PET and/or pericardium. The pericardium may be of the same material as the leaflets. In some embodiments, the inner and outer skirts may partly overlap each other in a skirt overlap region in FIG. 12, and include non-overlapping portions extending axially above and below, respectively, the overlap region. The inner skirt may be advantageous in channel blood towards the leaflets and preventing leakage of blood through the interstices of the lattice structure. The outer skirt may be advantageous in preventing leakage of blood at the interface between the stent-valve and surrounding tissue. Providing both skirts, but with only partial overlap, may enable the advantages of both to be obtained, but also reducing full overlap of material (which would otherwise increase the thickness of material of the stent-valve, making it more difficult to compress the stent-valve to a small size). The partial overlap nevertheless enables a reliable seal to be achieved between the inner and outer skirts.

In use, viewed in one general aspect, at least a portion of the inferior crown (or other fixation section) 140*a* may be received and constrained by the first sheath 120. At least a portion of the stent-component 134 not covered by the first sheath 120 may be received and constrained by the second sheath 122. As explained earlier and described in more detail below, a method of releasing the stent-valve 12 may include moving the second sheath 120 to an open position in order to deploy the crown/superior crown 140*b*, followed by the support section 142, and finally the arches 144*a*. For example, these elements may be deployed on an aorta side of a native and/or failed valve. Thereafter, once the operator is satisfied with the position and/or function of the stent-valve 12 within the native anatomy, the first sheath 120 may be moved to its open position in order to deploy the inferior crown 140*a*. Simultaneously, the attachment elements 68 may release from the stent-holder 30, optionally under the effects of the member 50 provided in the holder 30.

In some embodiments, the arches may be configured for aligning the stent-valve with respect to an axis of the ascending aorta by contact with a wall of the ascending aorta. For example, the arches may be bendable independently of each other. The crown may be configured for engaging and/or seating against existing leaflets from an outflow side. The fixation section may be configured for engaging an existing annulus. Deploying the arches before the fixation section may permit self-alignment of the stent-valve by the action of the arches, before the fixation section deploys to anchor the stent-valve at the annulus of the existing valve.

It will be appreciated that the foregoing description is merely illustrative of preferred embodiments of the invention, and that many modifications, alternatives and improvements may be made within the scope and/or principles described herein.

The invention claimed is:

1. A delivery catheter for a prosthetic heart valve, the valve expandable from a collapsed condition for delivery to an expanded condition for implantation, the delivery catheter, comprising:

a holder for engaging the valve in the collapsed state of the valve;

wherein the holder includes an engagement region for engaging at least a portion of the prosthetic heart valve for restraining axial displacement of the prosthetic valve in at least one axial direction of the catheter when the valve is in the collapsed condition around the holder;

a sheath translatable with respect to the holder between a first position in which the sheath surrounds at least a first portion of the holder, and a second position in which the sheath does not surround the first portion of the holder and wherein the sheath translates in a longitudinal direction of the delivery catheter when moving from the first position to the second position;

a multi-limbed member part of the holder;

wherein the engagement region of the holder comprises one or more male and/or female engagement regions for mating and/or interlocking engagement with the prosthetic valve, and wherein the engagement region, and the multi-limbed member having at least one stop surface associated with the engagement region, are relatively movable with respect to each other; and an interface member on a longitudinal opposite side of the holder from the multi-limbed member for (i) bridging a gap between the holder and the sheath when in the second position, and/or (ii) defining a generally smooth interface surface between the holder and the sheath when in the second position.

2. The delivery catheter of claim 1, wherein the interface member is associated with the holder.

3. A combination of the delivery catheter of claim 2, and an expandable prosthetic valve for delivery by the catheter.

4. The delivery catheter of claim 1, wherein the interface member is compressible to a radially collapsed condition to fit within the sheath when the sheath is in the first position.

5. The delivery catheter of claim 4, wherein the interface member has a generally bulbous shape in the radially expanded condition, and a less bulbous shape in the radially collapsed condition.

6. The delivery catheter of claim 1, wherein the interface member has a cage structure comprising a plurality of struts.

7. The delivery catheter of claim 1, wherein the catheter comprises at least two sheaths over an accommodation region of the expandable prosthetic valve, wherein the first sheath of the at least two sheaths is the sheath that translates in the distal direction of the delivery catheter when moving from the first position to the second position; and the second sheath of the at least two sheaths is translatable in opposite proximal direction to its open position.

8. The delivery catheter of claim 7, wherein the first and second sheaths have the same inner diameter and/or the same outer diameter.

9. The delivery catheter of claim 7, wherein the first and second sheaths are configured not to overlap each other.

10. A delivery catheter for a prosthetic heart valve, the valve expandable from a collapsed condition for delivery to an expanded condition for implantation, the delivery catheter, comprising:

a holder for engaging the valve in the collapsed state of the valve, the holder including an engagement region for engaging at least a portion of the prosthetic heart valve for restraining axial displacement of the prosthetic valve in at least one axial direction of the catheter when the valve is in the collapsed condition around the holder;

a sheath translatable with respect to the holder between a first position in which the sheath surrounds at least a first portion of the holder, and a second position in which the sheath does not surround the first portion of the holder and wherein the sheath translates in a longitudinal direction of the delivery catheter when moving from the first position to the second position;

a multi-limbed member adjacent the holder; and an interface member on a longitudinal opposite side of the holder from the multi-limbed member for (i) bridging a gap between the holder and the sheath when in the second position, and/or (ii) defining a generally smooth interface surface between the holder and the sheath when in the second position;

wherein the engagement region of the holder comprises one or more male and/or female engagement regions for mating and/or interlocking engagement with the prosthetic valve, and wherein the engagement region, and the multi-limbed member having at least one stop surface associated with the engagement region, are relatively movable with respect to each other;

wherein the engagement region of the holder comprises at least one projection, and the at least one stop surface is movable to reduce the projection height of the projection.

11. A delivery catheter for a prosthetic heart valve, the valve expandable from a collapsed condition for delivery to an expanded condition for implantation, the delivery catheter, comprising:

a holder for engaging the valve in the collapsed state of the valve, the holder including an engagement region for engaging at least a portion of the prosthetic heart valve for restraining axial displacement of the prosthetic valve in at least one axial direction of the catheter when the valve is in the collapsed condition around the holder;

a sheath translatable with respect to the holder between a first position in which the sheath surrounds at least a first portion of the holder, and a second position in which the sheath does not surround the first portion of the holder and wherein the sheath translates in a longitudinal direction of the delivery catheter when moving from the first position to the second position;

a multi-limbed member adjacent the holder; and an interface member on a longitudinal opposite side of the holder from the multi-limbed member for (i) bridging a gap between the holder and the sheath when in the second position, and/or (ii) defining a generally smooth interface surface between the holder and the sheath when in the second position;

wherein the engagement region of the holder comprises one or more male and/or female engagement regions for mating and/or interlocking engagement with the prosthetic valve, and wherein the engagement region, and the multi-limbed member having at least one stop surface associated with the engagement region, are relatively movable with respect to each other;

wherein the at least one stop surface comprises an aperture through which a male engagement region of the holder can project.

* * * * *